(12) United States Patent
Finitsis

(10) Patent No.: US 8,449,566 B2
(45) Date of Patent: May 28, 2013

(54) THROMBUS REMOVAL SYSTEM AND PROCESS

(75) Inventor: Stephanos Finitsis, Thessaloniki (GR)

(73) Assignee: Nexgen Medical Systems, Inc., Reno, NV (US)

( * ) Notice: Subject to any disclaimer, the term of this patent is extended or adjusted under 35 U.S.C. 154(b) by 0 days.

(21) Appl. No.: 13/151,954

(22) Filed: Jun. 2, 2011

(65) Prior Publication Data

US 2011/0230908 A1 Sep. 22, 2011

Related U.S. Application Data

(63) Continuation of application No. 11/097,354, filed on Apr. 1, 2005, now Pat. No. 7,955,344.

(51) Int. Cl.
*A61B 17/22* (2006.01)
*A61B 17/3207* (2006.01)

(52) U.S. Cl.
CPC .................. *A61B 17/3207* (2013.01)
USPC .......................................... 606/159; 606/127

(58) Field of Classification Search
USPC ................ 606/200, 127, 113, 159, 192
See application file for complete search history.

(56) References Cited

U.S. PATENT DOCUMENTS

| | | | |
|---|---|---|---|
| 2,756,752 A | 7/1956 | Scherlis | |
| 3,174,851 A | 3/1965 | Buehler et al. | |
| 3,351,463 A | 11/1967 | Rozner et al. | |
| 4,429,724 A | 2/1984 | Dorros et al. | |
| 4,448,195 A | 5/1984 | LeVeen et al. | |
| 4,512,338 A | 4/1985 | Balko et al. | |
| 4,706,671 A | 11/1987 | Weinrib | |
| 4,827,931 A | 5/1989 | Longmore | |
| 4,922,924 A | 5/1990 | Gambale et al. | |
| 4,989,608 A | 2/1991 | Ratner | |
| 5,064,428 A | 11/1991 | Cope et al. | |
| 5,122,136 A | 6/1992 | Guglielmi et al. | |
| 5,154,179 A | 10/1992 | Ratner | |
| 5,211,166 A | 5/1993 | Sepponen | |
| 5,222,971 A | 6/1993 | Willard et al. | |
| 5,234,437 A | 8/1993 | Sepetka | |
| 5,250,071 A | 10/1993 | Palermo | |
| 5,261,916 A | 11/1993 | Engelson | |
| 5,304,195 A | 4/1994 | Twyford, Jr. et al. | |
| 5,312,415 A | 5/1994 | Palermo | |

(Continued)

OTHER PUBLICATIONS

Webster's New Universal Unabridged Dictionary, Second Edition, Library of Congress Catalog Card No. 83-42537, p. 1074; definition of "lumen."

(Continued)

*Primary Examiner* — Ryan Severson
*Assistant Examiner* — David Eastwood
(74) *Attorney, Agent, or Firm* — Mark A. Litman & Associates, P.A.

(57) ABSTRACT

A device captures and assists in the removal of a thrombus in arteries, even in small arteries. The device uses a soft coil mesh to engage the surface of a thrombus, and a guidewire is used to retract the soft coil mesh with the captured thrombus. The soft coil is formed by an elongated microcoil element that forms the helical elements of a macrocoil element. The microcoil element provides a relatively elastic effect to the helical element forming the macrocoil and allows for control of gripping forces on the thrombus while reducing non-rigid contact of the device with arterial walls.

19 Claims, 5 Drawing Sheets

U.S. PATENT DOCUMENTS

| | | | |
|---|---|---|---|
| 5,350,397 A | 9/1994 | Palermo et al. | |
| 5,354,295 A | 10/1994 | Guglielmi et al. | |
| 5,375,596 A | 12/1994 | Twiss et al. | |
| 5,522,819 A | 6/1996 | Graves et al. | |
| 5,527,338 A | 6/1996 | Purdy | |
| 5,649,949 A | 7/1997 | Wallace et al. | |
| 5,690,667 A | 11/1997 | Gia | |
| 5,720,735 A | 2/1998 | Dorros | |
| 5,744,958 A | 4/1998 | Werne | |
| 5,772,609 A | 6/1998 | Nguyen et al. | |
| 5,797,953 A | 8/1998 | Tekulve | |
| 5,851,206 A | 12/1998 | Guglielmi et al. | |
| 5,868,754 A | 2/1999 | Levine et al. | |
| 5,895,398 A | 4/1999 | Wensel et al. | |
| 5,972,019 A | 10/1999 | Engelson et al. | |
| 6,066,149 A | 5/2000 | Samson et al. | |
| 6,139,510 A | 10/2000 | Palermo | |
| 6,325,823 B1 | 12/2001 | Horzewski et al. | |
| 6,436,112 B2 | 8/2002 | Wensel et al. | |
| 6,500,185 B1 * | 12/2002 | Mathews et al. | 606/159 |
| 6,511,492 B1 | 1/2003 | Rosenbluth et al. | |
| 6,652,536 B2 | 11/2003 | Mathews et al. | |
| 6,656,201 B2 | 12/2003 | Ferrera et al. | |
| 6,676,627 B1 | 1/2004 | Bonnette et al. | |
| 6,805,684 B2 | 10/2004 | Bonnette et al. | |
| 6,855,136 B2 | 2/2005 | Dorros et al. | |
| 6,902,540 B2 | 6/2005 | Dorros et al. | |
| 6,929,634 B2 | 8/2005 | Dorros et al. | |
| 7,608,087 B1 | 10/2009 | Addis | |
| 2001/0031971 A1 | 10/2001 | Dretler et al. | |
| 2004/0039435 A1 | 2/2004 | Hancock et al. | |
| 2004/0098023 A1 | 5/2004 | Lee et al. | |
| 2004/0138692 A1 | 7/2004 | Phung et al. | |
| 2004/0225229 A1 | 11/2004 | Viola | |
| 2005/0038447 A1 | 2/2005 | Huffmaster | |
| 2005/0055034 A1 | 3/2005 | Bates | |
| 2005/0277976 A1 | 12/2005 | Galdonik et al. | |
| 2006/0064114 A1 | 3/2006 | Obitsu et al. | |

OTHER PUBLICATIONS

Dorland's Pocket Medical Dictionary, 21st Edition, 1968, Library of Congress Catalogue Card No. 98-578, p. 361; definintion of "lumen."

* cited by examiner

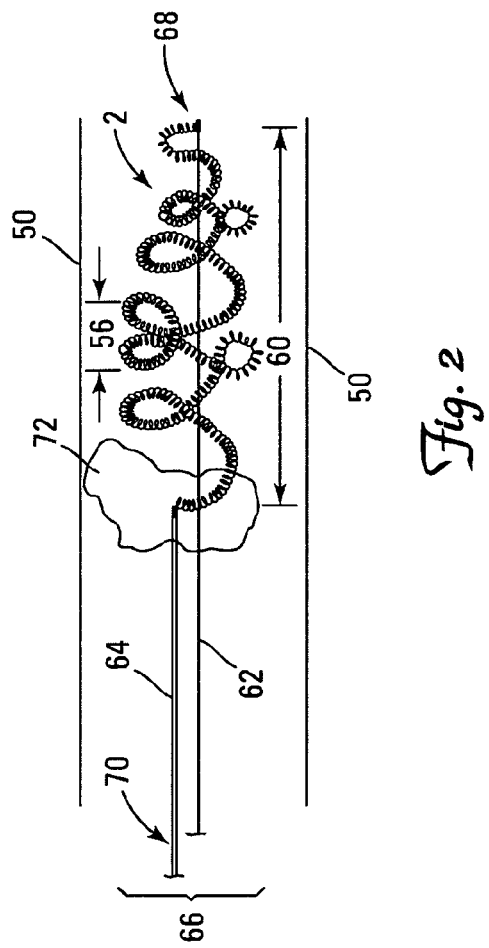
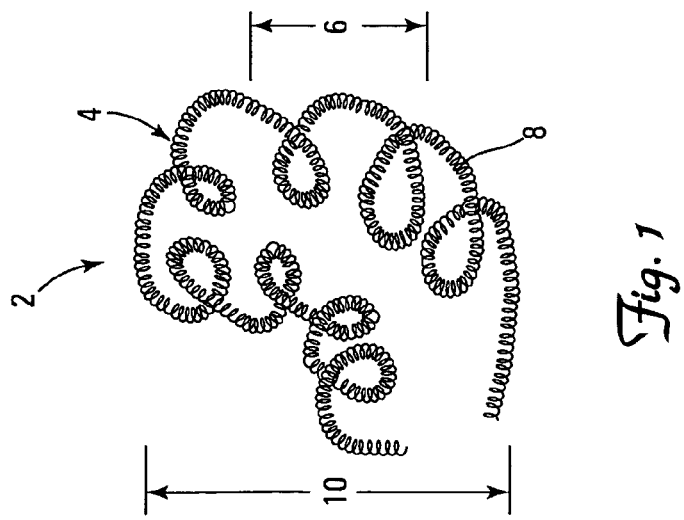

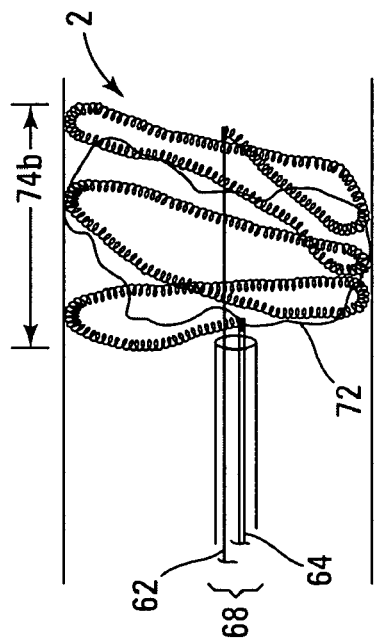
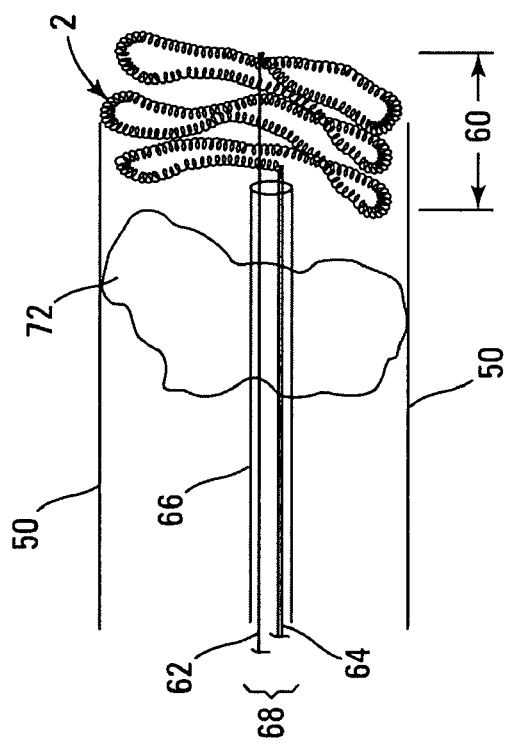

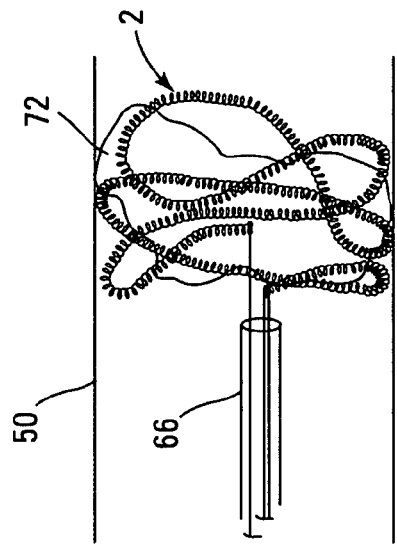
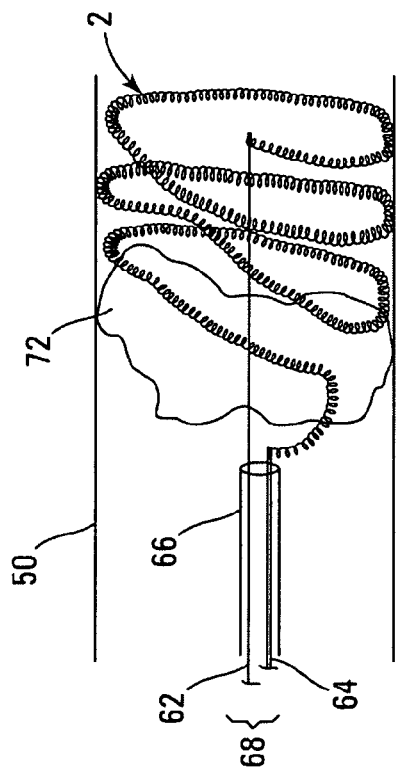
Fig. 4A
Fig. 4B

THROMBUS REMOVAL SYSTEM AND PROCESS

RELATED APPLICATION DATA

This application is a Continuation of U.S. patent application Ser. No. 11/097,354, filed Apr. 1, 2005, now U.S. Pat. No. 7,955,344.

BACKGROUND OF THE INVENTION

1. Field of the Invention

The present invention pertains to intravascular medical devices. More particularly, the present invention pertains to devices for capturing and removing blood clots from a blood vessel. This same system may also be used to remove material from other cavities of the body, for example, stones from the urinary or the biliary tract.

2. Background of the Art

The present invention pertains generally to thrombus collection and removal. Blood thrombus, may form a clot in a patient vasculature. Sometimes such clots are harmlessly dissolved in the blood stream. At other times, however, such clots may lodge in a blood vessel or embolize a distal blood vessel where they can partially or completely occlude the flow of blood. If the partially or completely occluded vessel feeds blood to sensitive tissue such as, the brain, lungs or heart, for example, serious tissue damage may result.

When symptoms of an occlusion are apparent, such as an occlusion resulting in a stroke, immediate action should be taken to reduce or eliminate resultant tissue damage. One approach is to treat a patient with clot dissolving drugs. These drugs, however, do not immediately dissolve the clot from the patient.

Published U.S. Patent Application 2005/0038447 describes A medical device for removing clots from a blood vessel, comprising: a first longitudinally-oriented spine having a distal end; a pushing member coupled to the proximal end of the first longitudinally-oriented spine and extending proximally therefrom; and a clot-grabbing basket generally disposed between and coupled to the first longitudinally-oriented spine.

Published U.S. Patent Application 2004/0138692 discloses an embolus extractor, comprising: an elongated shaft having a proximal end and a distal end; first and second struts, each strut having a proximal end and a distal end coupled to the distal end of the shaft; the first and second struts having a first position and a second position, wherein in the first position, the distal ends and the proximal ends of the struts are spaced at a first distance, and in the second position the distal ends and the proximal ends of the struts are spaced at a second distance, the second distance being less than the first distance; and third and fourth struts, each strut coupled to one of the first and second struts via a proximal end and distal end.

Published U.S. Patent Application 2004/0098023 discloses a vaso-occlusive device, comprising: a core member; and a fibrous structure carried by the core member, the fibrous structure comprises one or more strands of nanofibers. The vaso-occlusive device may provide the fibrous structure in a product generated at least in part by an electrospinning process comprises the steps of: supplying a polymer solution through a needle; electrostatically charging the needle; electrostatically charging a metal plate that is placed at a distance from the needle, the metal plate having a charge that is opposite that of the needle, thereby sending a jet of the polymer solution towards the metal plate; and collecting the fibrous structure from the metal plate.

Published U.S. Patent Application 2004/0039435 discloses a self-expanding, pseudo-braided device embodying a high expansion ratio and flexibility as well as comformability and improved radial force. The pseudo-braided device is particularly suited for advancement through and deployment within highly tortuous and very distal vasculature. Various forms of the pseudo-braided device are adapted for the repair of aneurysms and stenoses as well as for use in thrombectomies and embolic protection therapy.

There are a variety of ways of discharging shaped coils and linear coils into a body cavity. In addition to those patents that describe physically pushing a coil out of the catheter into the body cavity (e.g., Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device.

A variety of mechanically detachable devices are also known. Various examples of these devices are described in U.S. Pat. No. 5,234,437, to Sepetka, U.S. Pat. No. 5,250,071 to Palermo, U.S. Pat. No. 5,261,916, to Engelson, U.S. Pat. No. 5,304,195, to Twyford et al., U.S. Pat. No. 5,312,415, to Palermo, and U.S. Pat. No. 5,350,397, to Palermo et al.

Various configurations have been used to remove calculi from the biliary or urinary system. See, for instance, U.S. Pat. No. 5,064,428. Additionally, devices having various configurations have been used to remove objects from the vasculature. For example, surgical devices comprising one or more expandable and collapsible baskets have been described for removing or piercing a thrombus in the vasculature. See, U.S. Pat. No. 6,066,149. U.S. Pat. No. 5,868,754 describes a three prong-shaped device for capturing and removing bodies or articles from within a vessel.

Published U.S. Patent Application 2004/0225229 describes a device comprising a core wire having a distal end and a proximal end; a catheter shaft having a proximal catheter end, a distal catheter end and a lumen through which the core wire is passed such that the distal end of the core wire extends beyond the distal catheter end; a retrieval element disposed at the distal end of the core wire, the retrieval element movable from a radially contracted position to a radially expanded position; and a first stop element attached to the core wire, the first stop element configured to prevent over-expansion of the retrieval element.

Among commercial thrombus-removal systems are at least the following:
1) The MERCI system of Concentric Medical that has a form of a corkscrew or helix spring. In this system, which may use a large 0.018 F microcatheter, the microcatheter tip is first positioned across the thrombus with the help of a guidewire. Then the guidewire is exchanged with the system which is deployed distal and into the thrombus. The shape of the system allows it to get inserted into the thrombus. Then the thrombus is retrieved out of the artery into a large 9 French working catheter, and then out of the body.
2) The In-Time system of Boston Scientific which is a sort of a clam-shell guide, that once placed through the thrombus divides itself into 4 strings that form an oval, as with a rugby balloon. The system is pulled back to carry out the thrombus. This is similar to the disclosed structure in Published US Application 2004/0138692.
3) Another system is what is called a lasso, which is a simple catheter with a wire attached to its end. This wire makes a loop and enters back into the catheter (e.g., a large 0.018 F microcatheter). The operator changes the aspect of the loop by pulling on the wire. This system was originally conceived to catch foreign bodies.

4) The Catch system of Balt is a stent closed on one end and forming a basket that is deployed distal to the thrombus. The operator then pulls the system and retrieves the thrombus. This is similar to the structure in FIG. 7 of U.S. Pat. No. 6,805,684.

The above systems may have various disadvantages, such as either to slide on the thrombus, either to fractionate, to be difficult to guide or deploy or to be traumatic to the artery while some of them are quite expensive. In addition, all these system are bulky and cannot be used in small caliber arteries.

SUMMARY OF THE INVENTION

A device capable of capturing and assisting in the removal of a thrombus in arteries, and even in small arteries uses a soft coil mesh to engage the surface of a thrombus, and a guidewire is used to retract the soft coil mesh with the captured thrombus. The soft coil is formed by an elongated microcoil element that forms the helical elements of a macrocoil element. The microcoil element provides a relatively elastic effect to the helical element forming the macrocoil and allows for control of gripping forces on the thrombus while reducing non-rigid contact of the device with arterial walls.

BRIEF DESCRIPTION OF THE FIGURES

FIG. 1 shows the microcoil/macrocoil structure of the soft coil capture device described herein.

FIG. 2 shows a soft coil capture device in an insertion position within an artery.

FIG. 3A shows a soft coil capture device in a pre-capture position within an artery in a first mode of soft coil delivery.

FIG. 3B shows a soft coil capture device in a thrombus engaged position within the first mode of soft coil delivery of FIG. 3A.

FIG. 4A shows a soft coil capture device in a pre-capture position within an artery in a second mode of soft coil delivery.

FIG. 4B shows a soft coil capture device in a thrombus capture position within an artery within the second mode of soft coil delivery of FIG. 4A.

DETAILED DESCRIPTION OF THE INVENTION

Figure 5:
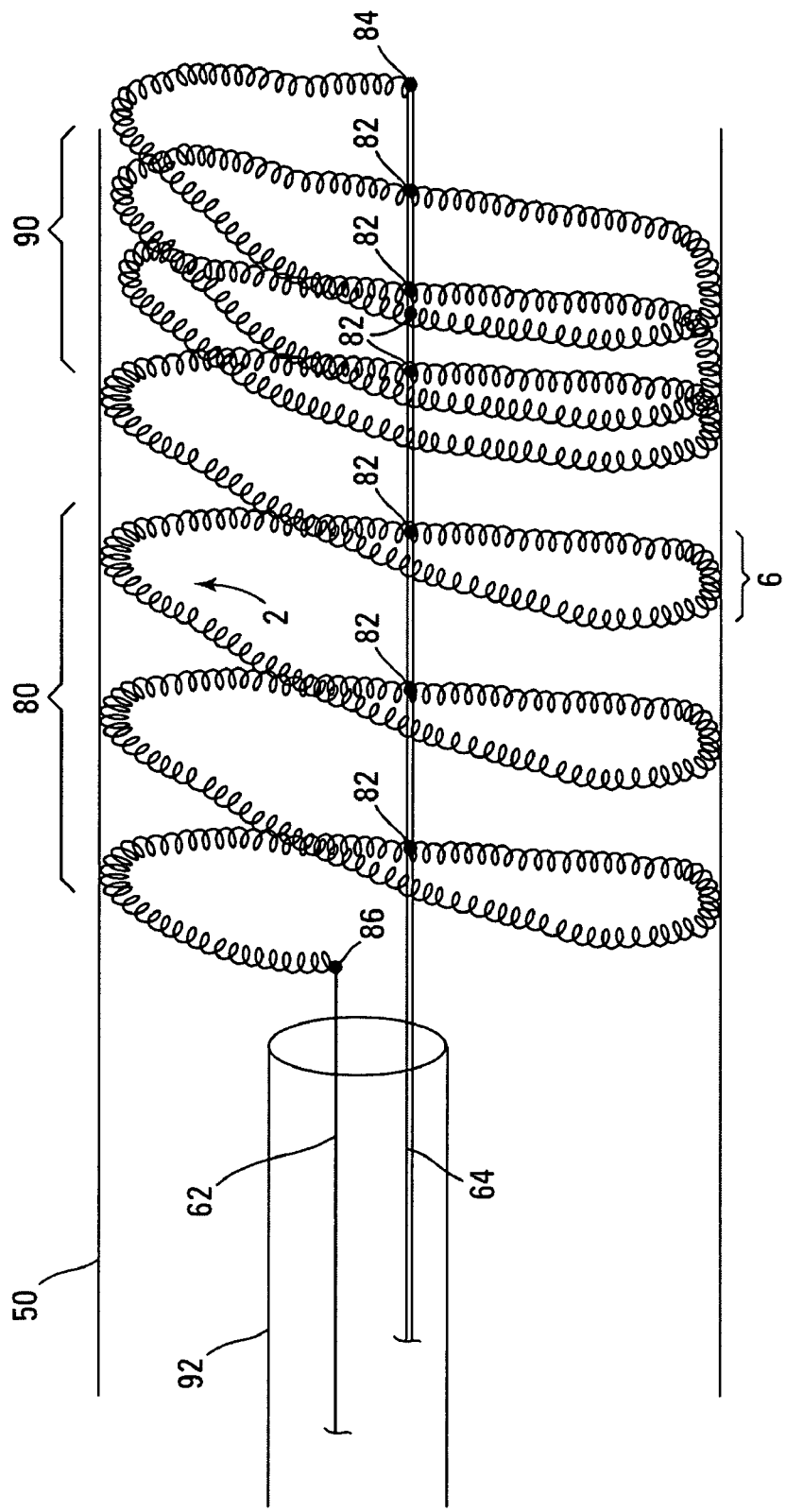
FIG. 5 shows a soft coil capture device (which may be of larger dimensions than parenchymal vasculature delivery devices) midway through deployment.

The following description should be read with reference to the drawings wherein like reference numerals indicate like elements throughout the several views. The detailed description and drawings illustrate example non-limiting specific embodiments of the generic claimed invention.

FIG. 1 shows a structural material 2 that can be used as a soft coil capture element in the practice of the technology described herein. The material 2 has microcoils or microloops forming a continuing chain 6 of microcoils that form the macrcoil or macrohelix 10. The term 'microcoil' as used herein should not be confused with the RF or MRI responsive coils or microcoils that are used in the medical imaging art. These are microcoils in the sense that they are small coils as compared to the macrocoils 10 which are large coils. The microcoils are made from structural material 8 that forms the filaments, threads, fibers, or the like that are used to provide the microcoils that build into the macrocoils. The benefits of this material and the structure in which they perform will become apparent from the discussion herein. The macrocoil and the microcoil can comprise non-thrombogenic compositions.

The microcoils add a significant degree of compliance, effective elasticity and cushioning ability to the macrocoil. The microcoils elongate to give the appearance of elasticity to the material 2, without providing hard and large abrasive surfaces that would contact arterial walls, as would traditional coil or mesh structures.

FIG. 2 shows the soft coil material 2 within an artery 50. The macrocoils 56 are shown with the entire length of the coil section 60 of the device being shown in a slightly extended position that is useful for insertion of the device 66. The pusher wire or guidewire 66 stabilizes the insertion end 68 of the soft coil material 2 while a pull wire 64 stabilizes the back end 70 of the device 66 and the material 2. The push wire 62 tends to be thicker than the pull wire 64 as a matter of course, but they may be of the same or similar thicknesses, and the pull wire may be thicker than the push wire 62. A thrombus 72 is shown, with the distended coil section 60 having been pushed past the thrombus 72.

FIG. 3A shows a first mode of delivery of the system 68 wherein the pulling wire 62 has been extended from the microcatheter 66 past the thrombus 72, and the push wire 64 has been slightly extended beyond the thrombus, being carried by the microcatheter 66. The pulling wire 62 and the push wire 64 are sufficiently close together so that the entire length of the extended coil 60 is restrained, but beyond the major mass of the thrombus 72. FIG. 3B shows the microcatheter 66 having been withdrawn from past the thrombus 72, the push wire also pulled rearward of the thrombus 72, and the end of the pulling wire 62 being retracted to pull the soft coil material 2 into a tangled engagement with the thrombus, engaging the thrombus 72 so that withdrawal of the microcatheter and the two wires 62 and 64 will withdraw the thrombus 72 while enmeshed in the soft coil material. The entire enmeshing length 74b of the soft coil securely entrains the thrombus 72, and the soft coil material 2 assists in reducing breakage of the thrombus 72 and damage to vascular walls.

FIG. 4A shows the system 68 delivered in a second delivery mode, without the microcatheter 66 passing the thrombus 72 mass, where both the push wire 64 and the pull wire 62 are positioned so that the push wire 64 restrains the soft coil material 2 relatively in front of the thrombus 72 and the pulling wire 62 has been extended from the microcatheter 66 to employ the soft coil material 2. FIG. 4B shows that the pulling wire 62 has been retracted slightly, causing the soft coil material 2 to engage the thrombus 72 and enmesh the thrombus 72 within the soft coil material. By withdrawing the microcatheter 66, and the two wires 62 and 64, the thrombus can be withdrawn from the vessel 50 with minimal damage to the vessel 50 and reduced breakage in the thrombus 72. The nature of the mixture of the microcoils and macrocoils causes a constriction of the material around the thrombus, without segmenting (cutting) the thrombus easily, and without providing a cage surface that is as potentially damaging to arterial walls as are other structures used for thrombus retrieval and capture. The push wires and pull wires may be of equal wire dimensions (e.g., diameters) or different dimensions, with either one being thicker than the other in different embodiments.

The system is made of a 3D soft coil such that when the system gets deployed, it has the tendency to form a three dimensional cage, with loops of microcoils extending across the diameters of the arterial interior to assure that loops will be able to engage a thrombus when the loops are retracted. The ends of the coils may be attached on either its proximal end to a pusher wire and to its distal end to a very fine wire or visa versa. The entire system tends to be able to be provided in a very thin format (although the size may vary depending upon the need for fit within particular arterial passages, and can fit into a 0.010 Fr microcatheter or smaller. Both wires exit at the proximal end of the microcatheter and can be manipulated by the operator. First the microcatheter is positioned across the thrombus with the help of a microguidewire. Once the distal end of the microcatheter lies beyond the thrombus (usually while it is in a distended state, fairly elongate and narrow), the microguidewire is exchanged with the thrombus retrieval system. The thrombus retrieval system is activated and deployed so that a significant portion of the entire length of coil (e.g., ⅕, ¼ or one third of the coil) is positioned distal to the thrombus. A remaining significant portion of the coil (using, by way of non-limiting examples of amounts, with one third distal to or past the thrombus), such as at least ⅕, at least ¼ or one third or more of the coil length is wrapped around or codistant with (within the artery) the thrombus and ¼, ⅕ or one third or more proximal to the thrombus. Once the coil is deployed with a significant portion at least at the distal end of the thrombus and more desirably a significant portion past the distal end of the thrombus, the operator pulls the thin distal wire or pushes the thick proximal wire, so that the mesh of coil loops that has formed around the thrombus or expanded beyond the thrombus retracts on itself and grabs securely the thrombus. The thrombus now can be pulled out of the artery by pulling the microcatheter, the pusher wire and the thin distal wire on the same time out of the artery.

One other advantage of the system (in addition to what has been described already) is its very small size so it can retrieve thrombus from very small arteries, its capacity to pull out the thrombus in one piece, and its softness, allowing manipulation without trauma to the vessel wall. Larger versions have the advantage of retrieving a very large thrombus in one piece. This system may be used in any vessel of the body for the retrieval of thrombus or other material like foreign bodies.

The distal end of the soft coil material (where the pulling wire is attached) may be limited in its ability to extend away from the proximal end of the soft coil material (where the push wire is attached) by using an internal connector, such as a thread, that attaches to both ends of the soft coil, and provides a physical limit to how far the coil may be distended.

Whatever the consistency of the clot, i.e., soft or hard, once someone has passed the clot with the microcatheter, the distal mesh of coils when deployed will form a "sponge" or "piston" that should bring back at least a large part of the thrombus. It is also likely that the loops of the coil should prevent the loss of parts of the thrombus if it breaks into pieces. The tendency of the system to break soft thrombus will depend on characteristics such as the soft coil material thickness, the microcoil thickness the macrocoil thickness, density of the macrocoil, the 3D configuration of the macrocoils and the loop diameter of the coil. Even in the worst case envisioned, one could only deploy a distal and a proximal mesh or use a flow reversing system.

For a number of reasons, it may be desirable to capture and/or remove clots from the vasculature. The blood vessel can be essentially any vessel or even duct. The device may include two or more longitudinal wires, for example a guidewire, a push wire and a pull wire, as well as other functional wires (e.g., conductive wires for other features provided with the device, such as a resistive wire to enable heating of the coils, if conductive/resistive. The basket member or region of soft coils is attached to or otherwise coupled with the wires. In general, the device (wires and soft coil material) can be advanced through the vasculature to a suitable location, for example adjacent a clot, and expanded (when past or adjacent to the clot, so that the clot may be captured in the soft coils, upon operator action, and the captured clot can be removed from the vasculature.

The device may be configured to shift between a first generally collapsed configuration and a second generally expanded configuration, especially by the elastic memory of the coil material, and the guidance imposed by the at least two wires. In at least some embodiments, shifting between these configurations includes the longitudinal movement of one or both of the wires relative to one another. Movement of the wires may occur in either the proximal or distal direction and, in the case of both wires moving, may be in the same or opposite directions. Shifting may also result in one or both of the wires moving somewhat laterally (especially with distally controlled wires on the coil material (e.g., with materials that bend when heated, or the like, and a heating element attached thereto) so that the wires become closer or move apart one another.

Shifting between the collapsed and expanded configurations may occur in a number of differing manners. For example, the device or portions thereof may be made of a shape-memory material (such as nickel-titanium alloy or oriented coils) that can assume a pre-defined shape when unconstrained or when subjected to particular thermal conditions. According to this embodiment, the device can be manufactured to be "self-expanding" (when the longitudinal distension and restraint by the wires is removed) so that it can be delivered in a collapsed configuration then shift to the expanded configuration when a constraint is removed (e.g., the distal ends of the two wires brought closer together) or when the device is subject to the natural thermal conditions within blood vessel. Alternatively, shifting may occur by mechanically moving one or both of wires. Moving the wires may occur in a number of different ways such as by moving one or other of the wires attached to the distal or proximal end of the coil material on the device.

As described above, all or portions of the device (including but not limited to the coil materials and the wires) may be manufactured from polymeric, metallic, natural (e.g., gut wires), synthetic, or composite materials. Preferred materials tend to be polymeric, metallic, composite or mixtures or combinations of these materials. A conventional medical structural material such as nickel titanium alloy may be employed. However, any suitable material may be used including metals, metal alloys, polymers, etc. Some examples of suitable metals and metal alloys include stainless steel, such as 304V, 304L, and 316L stainless steel; linear-elastic or super-elastic nitinol or other nickel-titanium alloys, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material.

Some examples of suitable polymers may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example a polyether-ester elastomer such as ARNITEL® available from DSM Engineering Plastics), polyester (for example a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene (PE), Marlex high-density polyethylene, Marlex low-density polyethylene, linear low density polyethylene (for example REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and the like. In some embodiments, portions of or all of the device can be blended with a liquid crystal polymer (LCP). For example, the mixture can contain up to about 5% LCP.

In some embodiments, a coating, for example a lubricious, a hydrophilic, a protective, or other type of coating may be applied over portions or all of the device. Hydrophobic coatings such as fluoropolymers provide a dry lubricity which improves device exchanges. Lubricious coatings improve steerability and improve lesion crossing capability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the sheath or coating may be applied over basket region. This may provide extra surface area to contain clots that might be captured therein.

The sheath or polymeric layer coating may be formed, for example, by coating, electrophoresis, by extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

The device, or portions thereof, may also be coated, plated, wrapped or surrounded by, doped with, or otherwise include a radiopaque material. For example, the wires or coils may be made from a radiopaque material or may include a radiopaque marker member or coil coupled thereto. Radiopaque materials are understood to be materials capable of producing a relatively bright image on a fluoroscopy screen or another imaging technique during a medical procedure. This relatively bright image aids the user of the device in determining its location. Some examples of radiopaque materials can include, but are not limited to, gold, platinum, palladium, tantalum, tungsten alloy, plastic material loaded with a radiopaque filler, and the like.

In some embodiments, a degree of MRI compatibility may be imparted into the device. For example, to enhance compatibility with Magnetic Resonance Imaging (MRI) machines, it may be desirable to make portions of the device, in a manner that would impart a degree of MRI compatibility. For example, the device, or portions thereof, may be made of a material that does not substantially distort the image and create substantial artifacts (artifacts are gaps in the image). Certain ferromagnetic materials, for example, may not be suitable because they may create artifacts in an MRI image. The device, or portions thereof, may also be made from a material that the MRI machine can image. Some materials that exhibit these characteristics include, for example, tungsten, Elgiloy, MP35N, nitinol, and the like, and others.

The control wire(s) may be produced from any number of suitable materials having reasonable strength in tension, e.g., stainless steels, carbon fibers, engineering plastics, tungsten alloys, variously in the form of a multi-strand cable or single strand thread. Preferably, however, the wire may be made from a "so-called" super-elastic alloy. These alloys are characterized by an ability to transform from an austenitic crystal structure to a stress-induced martensitic (SIM) structure and to return elastically to the austenitic crystal structure (and the original shape) when the stress is removed. A typical alloy is nitinol, a nickel-titanium alloy, which is readily commercially available and undergoes the austenite-SIM-austenite transformation at a variety of temperature ranges. These materials are described, for instance in U.S. Pat. Nos. 3,174,851 and 3,351,463. These alloys are especially suitable because of their capacity to elastically recover almost completely to the initial configuration once the stress is removed. Since this is so, the size of the actual wire may be made fairly small, e.g., as small as 0.005 inches in diameter or smaller, and the resulting device is able to access very small regions of the body. The wire may also vary in diameter along its length, for example have a larger diameter at the proximal end as compared to the distal end or vice versa.

The wires can have a proximal section and a distal section. The proximal section preferably has a uniform diameter of at least about 0.0001 inch, or about 0.005 to 0.025 inches, preferably 0.0010 to 0.018 inches. Commercially available wires with a microcoil (wire) diameter of 0.008 mm and a macrocoil diameter of 1 mm are available as microcoil materials. Optionally, the distal section may have different (more or less) flexibility than the proximal section and extends beyond the catheter. Typically, both sections will extend from the distal and proximal ends of the catheter lumen. The wire may have a middle section having a diameter intermediate between the diameter of the two portions of the wire adjoining the middle section or the middle section may be continuously tapered, may have a number of tapered sections or sections of differing diameters, or may be of a uniform diameter along its length and be tapered at or near the distal section. The entire wire may be between about 50 and 300 cm, typically between about 175 to 190 cm in length. The wire may be wrapped to form a coil section or may be independently attached to a coil.

The overall length of the control wire may extend through a catheter and the wire and catheter inserted into the vasculature. The catheter and wires (with attached soft coil may extend proximal or distal to the site of the clot or the catheter may be positioned and the wires extend to the site from the catheter. The configurable soft coil component of the device is positioned near the target thrombus site, and the wires position and control the positioning and attitude of the soft coil capture components.

FIG. 5 shows a soft coil capture device 4 (which may be of larger dimensions than parenchymal vasculature delivery devices) midway through deployment. In small coils, but particularly with larger coils, greater strength may be built into the elastic memory of the material 2 and the macrocoils 6 and the length of remembered coil distribution 80. The coil material 2 may be delivered through a catheter 92, with the elongation of the coils 2 controlled by relative positioning of the push and pull (guide) wires 62 and 64 as explained above. One end of the coil material 2 is shown secured to the push wire 86 and the distal (leading end) of the coil material 2 is shown secured to the distal end of the pull (guide) wire 64. When in a fully deployed region 80, without tension or retension applied by the wires 62 and 64, a natural distribution (frequency) of the macrocoils 6 will exist. Points of contact 82 between the coils 6 and the pull (guide) wire 64 are preferably not secured to the wires 62 and 64, but are able to slide freely against them. If the contact points were secured, the frequency between the coils would be fixed before and after deployment, unlee the pull (guide) wire 64 were able to telescope or otherwise extend. As shown in the figure, the macrocoils 6 when in a deploying region 90, without restraining action through the connection at the distal connecting point 84 has a greater frequency (less spacing) between the macrocoils 6. The macrocoils 6 are shown being deployed out of a catheter 92. The microcoils and macrocoils may be manufactured and designed so as to provide nature dimensions when tension is released after deployment to fit a range of dimensions in vasculature. The selection of the microcoil size, macrocoil spacing, wire thickness, wire material, macrocoil size and macrocoil spacing are used to determine the frequency, size and shape of the deployed structure.

Figure 6:
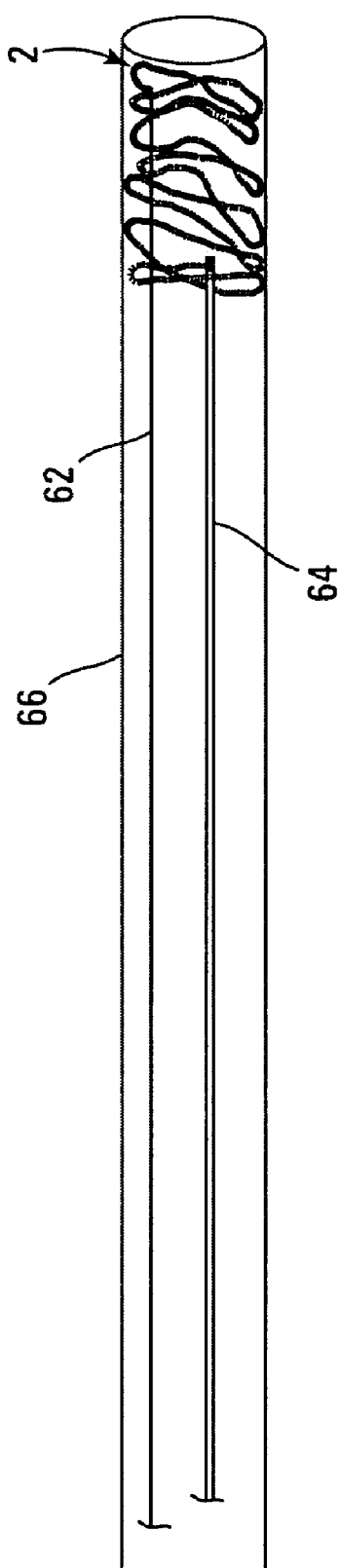
FIG. 6 shows a microcatheter delivery system with constrained coils within the microcatheter.

FIG. 6 shows a microcatheter 66 having the pull wire 62 and the push wire 64 with the soft coil material 2 completely within the confines of the microcatheter 66. The soft coil material will deploy, expanding under its elastic compressive tension, to the limits of its size or the limits of space within the vasculature when the two wires 62 and 64 force the soft coil material from within the microcatheter 66. In actual delivery of the system, the soft coil material may be present within the microcatheter in a relatively more linear distribution of the microcoils within the lumen of the catheter, rather than as the combination of macrocoils and microcoils shown.

Although the examples show specific dimensions and materials, the examples and descriptions are not intended to be limiting to the scope of practice and protection of the technology described. Rather, any specific statements or values are intended to be examples within the generic concepts of the inventions and the disclosure taught and provided herein.

What is claimed:

1. A medical device for removing a thrombus from a blood vessel, comprising: a catheter having a first lumen; within the first lumen of the catheter is a macrocoil thrombus engaging component having a length with a proximal end and a distal end, the length of the macrocoil comprising microcoils that allow the length of the macrocoil to be extendable; within the first lumen is a first wire capable of providing force on the distal end of the macrocoil; within the first lumen is a second wire capable of providing force on the proximal end of the macrocoil; the macrocoil being capable of completely retracting within the first lumen of the catheter to a maximum thickness that is less than one half of a diameter of the macrocoil when extended out of the first lumen of the catheter by the first wire and the second wire being pulled from within the first lumen, and the microcoil being expandable to a width of at least 0.002 mm when distended by relative movement between the first wire and second wire, wherein the medical device has only a single lumen.

2. The medical device of claim 1 wherein the macrocoil and the microcoil comprise non-thrombogenic compositions.

3. The medical device of claim 1 wherein the first wire on the proximal end of the macrocoil has a different thickness than the second wire on the distal end of the macrocoil and the medical device has only a single lumen.

4. The medical device of claim 1 wherein the first wire on the proximal end of the macrocoil and the second wire on the distal end of the macrocoil have the same thickness and the device has only a single lumen.

5. The medical device of claim 1 wherein the macrocoil and first and second wire are located within the catheter having a diameter enabling the catheter's insertion into an artery of a human being.

6. The medical device of claim 2 wherein the macrocoil and first and second wire are located within the catheter having a diameter enabling the catheter's insertion into an artery of a human being.

7. The medical device of claim 3 wherein the macrocoil and first and second wire are located within the catheter having a diameter enabling the catheter's insertion into an artery of a human being.

8. The medical device of claim 1 wherein when the macrocoil has been removed from within the catheter, the microcoils are adjacent equal size coils forming an elongate element and the elongate element outside of the catheter is formed into loops.

9. The medical device of claim 2 wherein when the macrocoil has been removed from within the catheter, the microcoils are adjacent equal size coils forming an elongate element and the elongate element outside of the catheter is formed into loops.

10. The medical device of claim 3 wherein when the macrocoil has been removed from within the catheter, the microcoils are adjacent equal size coils forming an elongate element and the elongate element outside of the catheter is formed into loops.

11. The medical device of claim 4 wherein when the macrocoil has been removed from within the catheter, the microcoils are adjacent equal size coils forming an elongate element and the elongate element outside of the catheter is formed into loops.

12. The medical device of claim 5 wherein when the macrocoil has been removed from within the catheter, the microcoils are adjacent equal size coils forming an elongate element and the elongate element outside of the catheter is formed into loops.

13. The medical device of claim 6 wherein when the macrocoil has been removed from within the catheter, the microcoils are adjacent equal size coils forming an elongate element and the elongate element outside of the catheter is formed into loops.

14. The medical device of claim 1 wherein when the macrocoil has been extended outside of the catheter, the macrocoil is configured to surround a thrombus and the microcoils are extended to conform the macrocoil to the thrombus and the device has only a single lumen.

15. The medical device of claim 4 wherein when the macrocoil has been extended outside of the catheter, the macrocoil is configured to surrounded a thrombus and the microcoils are extended to conform the macrocoil to the thrombus.

16. The medical device of claim 8 wherein when the macrocoil has been extended outside of the catheter, the macrocoil is configured to surrounded a thrombus and the microcoils are extended to conform the macrocoil to the thrombus.

17. The medical device of claim 10 wherein when the macrocoil has been extended outside of the catheter, macrocoil is configured to surrounded a thrombus and the microcoils are extended to conform the macrocoil to the thrombus.

18. The medical device of claim 12 wherein when the macrocoil has been extended outside of the catheter, and the macrocoil is configured to surrounded a thrombus and the microcoils are extended to conform the macrocoil to the thrombus.

19. A medical device for removing a thrombus from a blood vessel, comprising: a catheter having a first lumen; within the first lumen of the catheter is a macrocoil thrombus engaging component having a length with a proximal end and a distal end, the length of the macrocoil comprising microcoils that allow the length of the macrocoil to be extendable; within the first lumen is a first wire capable of providing force on the distal end of the macrocoil; within the first lumen is a second wire capable of providing force on the proximal end of the macrocoil; the macrocoil being capable of completely retracting within the first lumen of the catheter to a maximum thickness that is less than one half of a diameter of the macrocoil when extended out of the first lumen of the catheter by the first wire and the second wire being pulled from within the first lumen, and the microcoil loops being expandable to a width of at least 0.002 mm when distended by relative movement between the first wire and second wire, the medical device being free of resistive heating elements on the first wire and the second wire.

\* \* \* \* \*